United States Patent
Marki et al.

(10) Patent No.: US 9,074,919 B2
(45) Date of Patent: Jul. 7, 2015

(54) METHOD OF DEVICE FOR TESTING A CAPACITIVELY OPERATING MEASURING DEVICE, WHICH IS DESIGNED FOR THE DETECTION OF PHASE BOUNDARIES, AND CORRESPONDINGLY EQUIPPED LABORATORY APPARATUS

(75) Inventors: Sarah Marki, Zurich Schweiz (CH); Nicolas Cors, Stafa (CH); Thomas Struchen, Oetwil am See Schweiz (CH)

(73) Assignee: Tecan Trading AG, Mannedorf (CH)

( * ) Notice: Subject to any disclaimer, the term of this patent is extended or adjusted under 35 U.S.C. 154(b) by 575 days.

(21) Appl. No.: 13/487,650

(22) Filed: Jun. 4, 2012

(65) Prior Publication Data
US 2012/0304732 A1 Dec. 6, 2012

(30) Foreign Application Priority Data

Jun. 3, 2011 (CH) ........................ 0940/11

(51) Int. Cl.
*G01F 25/00* (2006.01)
*G01F 23/26* (2006.01)
*G01N 35/00* (2006.01)
*G01N 35/10* (2006.01)

(52) U.S. Cl.
CPC .......... *G01F 25/0076* (2013.01); *G01F 23/263* (2013.01); *G01F 23/265* (2013.01); *G01N 35/00623* (2013.01); *G01N 35/1011* (2013.01); *G01N 35/1065* (2013.01); *G01N 2035/1025* (2013.01)

(58) Field of Classification Search
None
See application file for complete search history.

(56) References Cited

U.S. PATENT DOCUMENTS

| | | | |
|---|---|---|---|
| 3,626,400 A | * | 12/1971 | Bates .......................... 340/516 |
| 4,441,157 A | * | 4/1984 | Gerchman et al. ............. 702/52 |
| 4,449,405 A | | 5/1984 | Franz et al. |
| 5,012,683 A | | 5/1991 | Davis |
| 5,365,783 A | | 11/1994 | Zweifel |
| 2006/0207322 A1 | | 9/2006 | Krufka et al. |
| 2007/0251341 A1 | | 11/2007 | Balmer |

FOREIGN PATENT DOCUMENTS

| | | |
|---|---|---|
| CH | 02011/09 | 12/2009 |
| DE | 102010049488 | 5/2011 |
| EP | 1116953 | 7/2001 |
| EP | 1380843 | 1/2004 |
| JP | 2003090754 | 3/2003 |
| WO | PCT/EP2010/070599 | 12/2010 |

\* cited by examiner

*Primary Examiner* — Robert R Raevis
(74) *Attorney, Agent, or Firm* — Notaro, Michalos & Zaccaria P.C.

(57) ABSTRACT

A device has at least one channel for detecting the phase boundary between media in a liquid container and has a probe which can be fed in the direction of the phase boundary and a circuit which processes a signal of the probe to detect a capacitance change. The device includes a testing module which executes an infeed movement of the probe. The testing module performs an analysis of the signal of the channel, and makes a connection statement about the electrical connection between the probe and the measuring circuit. The testing of the electrical connections is performed in a dry manner, i.e., a phase boundary does not have to be searched for or penetrated for the testing.

19 Claims, 7 Drawing Sheets

METHOD OF DEVICE FOR TESTING A CAPACITIVELY OPERATING MEASURING DEVICE, WHICH IS DESIGNED FOR THE DETECTION OF PHASE BOUNDARIES, AND CORRESPONDINGLY EQUIPPED LABORATORY APPARATUS

FIELD OF THE INVENTION

The invention is directed to a method for testing a capacitively operating measuring device, which is designed for the detection of phase boundaries, and correspondingly equipped laboratory apparatuses. In particular it is directed to a function test of such a measuring device and a laboratory apparatus, which are designed for detecting a liquid level in a liquid container.

BACKGROUND OF THE INVENTION

There are numerous laboratory systems and medical and pharmaceutical apparatuses in which it is important to ascertain the fill level in test tubes, microplates, or the like. There are also applications which relate to the detection of liquid-liquid phase boundaries. The term phase boundary is used hereafter both for transitions between gaseous and liquid media (gas-liquid phase boundary) and for transitions between various liquid media (liquid-liquid phase boundary).

In particular if the automation of measuring or experimental sequences is a goal, such an ascertainment of the phase boundary is significant. The fill level ascertainment is typically performed by means of a detection of the liquid level, i.e., the location of the phase boundary between air and liquid is ascertained. This procedure is also referred to as "liquid level detection" (LLD).

Liquid level detection is used, for example, in pipetting devices. Since a gas and a liquid have significantly different dielectric constants, the gas-liquid phase boundary can be determined via a capacitance change.

The detection of liquid-liquid phase boundaries plays an important role, e.g., during a liquid-liquid extraction. It is often important to know the exact phase boundary between aqueous and organic phases. Since non-miscible liquids have significantly different dielectric constants, the liquid-liquid phase boundary can be determined via a capacitance change. This can be used for the purpose of pipetting off an intermediate phase, for example.

In recent years, laboratory apparatuses have become more and more precise and complex. The trend is moving in the direction of higher integration, automation, and parallelism. This results in a high spatial compaction of the individual components and a shortening of the measurement sequences with respect to time. This compaction not only causes mechanical and other design problems, but rather also the precision of the electronic analyzing capability, the mutual influence of adjacent measuring channels, and other aspects may result in problems.

Figure 1:
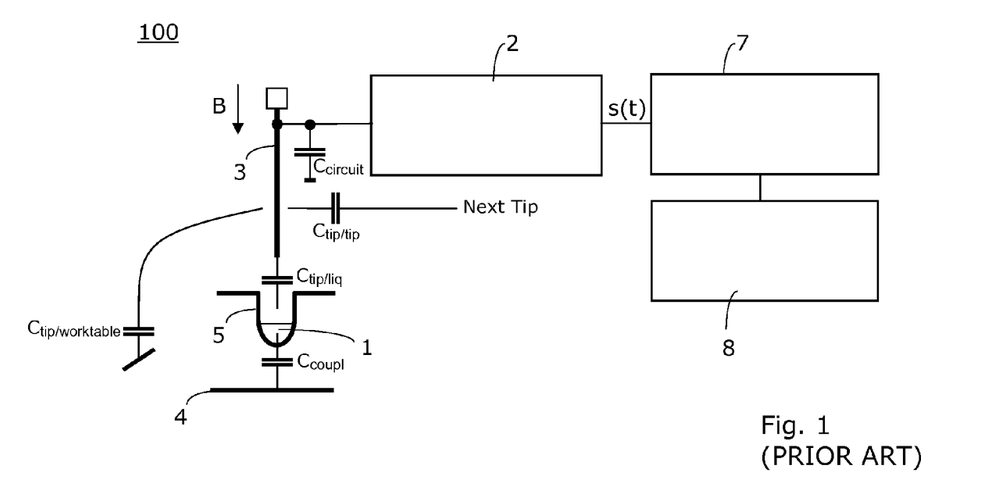
FIG. 1 shows a schematic side view of a laboratory apparatus according to the prior art.

The detection of a phase boundary is typically performed capacitively, as is schematically shown on the basis of FIG. 1. FIG. 1 shows the construction of a known laboratory apparatus 100, which is designed here for detecting a liquid level. The presence of a liquid 1 or the phase boundary between air and liquid 1 is detected here, e.g., by the observation of a capacitance change in $C_{tip/liq}$ and in the serial capacitance $C_{coupl}$. An electronic charging/discharging circuit 2 ensures charging and discharging, to be able to measure the effective capacitance between a probe, e.g., in the form of a pipette tip 3, and a grounded base plate 4. The signal processing can be performed using a signal processing circuit 7, which is assisted, e.g., by a controller 8.

The effective capacitance, which results depending on the laboratory apparatus 100 from the stray capacitances, electrical couplings through the probe or the pipette tip 3, the conductivity of the liquid 1, and the crosstalk between adjacent measuring channels (referred to as next tip in FIG. 1) is very small. It is typically in the range of a few Picofarad (pF). The capacitance change, which results upon plunging from the air into a liquid is once again less by approximately a factor of 100 to 1000.

Figure 2:
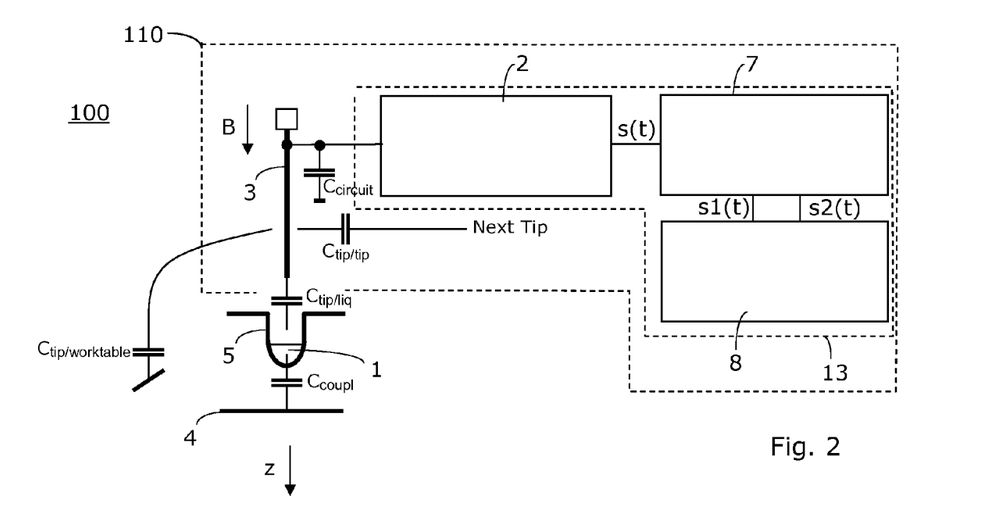
FIG. 2 shows a schematic side view of a device having a circuit according to a previously unpublished older application of the applicant of the present application, only the probe of a single channel being shown.

For the detection of phase boundaries, according to an older, but previously unpublished International Patent Application PCT/2010/070599, which was filed on 22 Dec. 2010 claiming the priority of Swiss Patent Application CH 02011/09 of 30 Dec. 2009, a multichannel, capacitively operating measuring device 110 is used. This measuring device 110 comprises, as shown in FIG. 2, one probe 3 (e.g., in the form of a conductive pipette tip or needle) per channel, which is fed into a liquid container 5 of the corresponding channel. During the infeed, a first signal s1(t) having short pulse width and a second signal s2(t) having greater pulse width are processed by a measuring circuit 8, to detect a phase boundary between two media in the liquid container 5 of the corresponding channel.

The device 110 is especially designed for detecting a liquid level (i.e., a gas-liquid phase boundary) in a liquid container 5. However, this device 110 may also be used for ascertaining other phase boundaries. For the purpose of detection, it comprises one probe 3 per channel, which can be fed in the direction of the liquid 1 into the liquid container 5. A circuit 13 having the circuit blocks 2, 7 and a measuring circuit 8, preferably in the form of a controller module, is used, which processes an output signal s(t) of the probe 3, in order to detect a capacitance change upon reaching or piercing the phase boundary. The circuit 13 comprises at least one first filter, in order to filter a first signal s1(t) having short pulse width out of the output signal s(t). In addition, the circuit 13 comprises a second filter, in order to filter a second signal s2(t) having greater pulse width out of the output signal s(t). The measuring circuit 8 has a comparator module, which is designed so that it can be ascertained whether the first signal s1(t) reaches a first threshold value T1. The first threshold value T1 is predefined by the device 110 or the laboratory apparatus 100. In addition to the first threshold value T1, the pulse width P1 can also be ascertained and/or analyzed. In addition, the measuring circuit 8 has a processing module, which is designed so that it can be ascertained whether the second signal s2(t) fulfills at least one predefined second signal criterion (e.g., a minimum slope ST, or a threshold value T2, or a pulse width P2).

Figure 3:
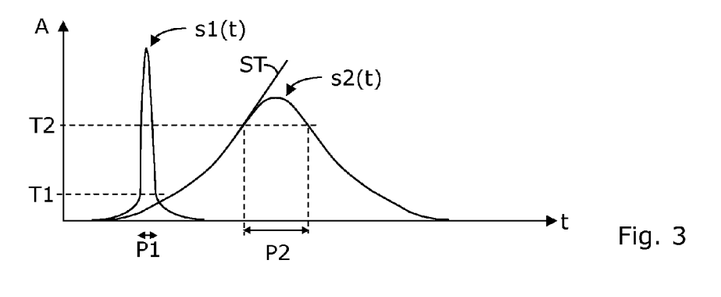
FIG. 3 shows a schematic amplitude-time graph in which two signals are shown in simplified form to be able to describe the application of criteria in a first device according to FIG. 2.

FIG. 3 shows a schematic amplitude-time graph, in which two signals s1(t) and s2(t), according to the technical teaching of International Patent Application PCT/2010/070599, of a normal measurement are shown in simplified form. The fundamental mode of operation of the device 110 will be described on the basis of this exemplary illustration. By splitting the signal s(t) by means of two filters into a first signal s1(t) and a second signal s2(t), a very precise statement is made possible. It is nonetheless possible to react immediately based on the first signal s1(t). Such an immediate reaction can be necessary, for example, after the detection of a signal s(t), which appears to be an immersion signal, to cause a stop of the infeed movement B, in order not to immerse more than necessary.

In FIG. 3, a first threshold value T1 is positioned at a relatively small amplitude A. In the simplest embodiment of the device 110, it is only ascertained whether the first signal s1(t) reaches this first threshold value T1. If this is the case, the first criterion for a detection is considered to be fulfilled here.

In FIG. 3, a second threshold value T2 is positioned at an amplitude A, which is above the first threshold value T1. It is now ascertained whether the second signal s2(t) fulfills at least one predefined second signal criterion. In the simplest embodiment of the device 110, it is only ascertained whether the second signal s2(t) reaches this second threshold value T2. If this is the case, the second criterion for a detection is considered to be fulfilled here.

If the first signal criteria and the second signal criteria are fulfilled, as described, the output of an identification (e.g., in the form of a signal or a code) can be performed, for example. This identification indicates that the device 110 has performed a detection of a liquid level.

The higher the degree of integration of such capacitively operating measuring devices, the more problematic it is to be able to recognize the capacitance changes to be measured because of stray capacitances, crosstalk between adjacent channels, and capacitance changes because of moving electrical supply lines.

After the final assembly of a laboratory apparatus, extensive quasi-real test runs for liquid level detection were heretofore performed. For this purpose, the worktable is equipped with mounts (so-called carriers), and with tubes, troughs, and microplates (so-called labware). The equipment of the worktable must be exactly simulated in the test software of the laboratory apparatus. The tubes and the depressions of the microplates (so-called wells) are filled with various volumes of water and water of differing conductivity (deionized water up to physiological table salt solution). In these test runs, the probes of the individual channels are guided successively or in combination with one another (all even/odd channels together, individually or all together) into the corresponding filled test tubes or wells and the signals are analyzed during this procedure. The sensitivity, the wiring, and the crosstalk are tested. A new set of pipette tips must be provided in each case for the individual tests or, if pipetting needles are used, the needles must be washed each time.

In the case of repair or service at the customer, a slightly reduced test program for liquid level detection is applied. Nonetheless, it has been heretofore unavoidable to change the customer-specific equipment of the worktable with carriers, to put on the test-specific carriers, and to reproduce the exact customer equipment after the test.

It is a disadvantage of this approach that the time and work expenditure is relatively large. It is important to fill the correct labware with the correct volume (=fill level) of the liquid having the correct conductivity. It is considered to be a further disadvantage that special worktable equipments having carriers and labware must be used.

With the increasing degree of automation of the laboratory apparatuses, it is additionally desirable to design the corresponding sequences so that it requires no or only little manual intervention. It is to be considered that, e.g., in automated pipetting systems or devices, numerous situations can occur, which cannot be resolved automatically by previous automated pipetting systems or apparatuses.

SUMMARY OF THE INVENTION

The object therefore presents itself of providing a device and a method for testing a capacitively operating measuring device, which is designed for the detection of phase boundaries. In addition, the object relates to providing a correspondingly equipped laboratory apparatus.

The method, or the measuring device or the laboratory apparatus, respectively, is preferably to be designed so that it independently recognizes critical situations or special cases and therefore as much as possible does not require manual or mechanical intervention during a test sequence.

These objects are achieved according to the invention by a method according to the claims, a device according to the claims, and a laboratory apparatus according to the claims.

In the case of a single-channel device, the following steps are executed to test the measuring device. An infeed movement of the probe of the one channel is executed during which step a signal is obtained from an output signal of the measuring device. A signal is obtained from an output signal of the measuring device. The signal of the channel of the measuring device is analyzed to be able to make a statement about the electrical connection (referred to as the connection statement) between the probe and the measuring circuit.

In the case of a multichannel apparatus, the following steps are executed to test the measuring device. An infeed movement of a probe of a single channel is executed while the probes of at least a part of the other channels, preferably the directly adjacent probes, are not moved. A signal is obtained from an output signal of the measuring device. The signal of the channel of the measuring device having moved probe and the signals of the channels having non-moved probes are analyzed to be able to make a statement (referred to as the connection statement) about the electrical connection between the probes and the measuring circuit.

According to the invention, either one signal is electronically analyzed, or multiple signals are electronically analyzed. A rapid signal (first signal) and a slow signal (second signal) are preferably filtered apart by a filtering method and electronically analyzed. More than two signals can also be filtered apart and electronically analyzed.

Corresponding signal-specific signal test criteria are preferably applied for analyzing the signal or signals.

According to the invention, during the test method, a probe is preferably moved downward and/or upward and a signal is analyzed or multiple signals are analyzed. The first rapid signals and the second slow signals are preferably analyzed.

The method according to the invention is particularly suitable for use in a multichannel device, which detects phase boundaries between media by means of multiple probes which can be fed in autonomously, the device detecting capacitance changes during movement of the probes in that it analyzes the signals, preferably first signals and second signals, after application of a filtering method.

The method is preferably used in a device or a laboratory apparatus, where the output signal at a probe has a potential of several volts and a frequency of several hundred kilohertz.

The method is preferably used in a device or a laboratory apparatus where the movement of a probe (relative path distance) is in the range between 10 mm and 200 mm.

The method is preferably used in a device or a laboratory apparatus where the movement of a probe at a slow speed is in the range between 10 mm/s and 200 mm/s and the rapid speed is in the range between 200 mm/s and 1000 mm/s.

The invention is designed for the purpose of being able to recognize various special cases, interfering variables, and influencing variables. The device or the laboratory apparatus is preferably designed so that it displays a reaction adapted to the situation.

It is an advantage of the present invention that various functions can be sequentially tested and various types of errors can be recognized. This is performed in all embodiments in a so-called contactless, or dry method, respectively, i.e., no liquid has to be touched during the performance of the testing method, or no plunging procedure must be executed. The method according to the invention is therefore referred to hereafter as a method for dry testing, in order to express this essential aspect. The testing of the electrical connections is performed according to the invention without touching a reference body or medium. The testing of the electrical connections is preferably performed according to the invention in a dry manner, i.e., no phase boundary must be searched for or penetrated for the testing.

The method of the invention is less time-consuming and susceptible to interference than previously known methods.

According to the invention, the required tests are performed in a contactless manner (preferably liquid-independent), so that the probe or probes are neither contaminated with liquids nor can the probes or their coating, respectively, be damaged by touching a solid contact surface.

According to the invention, no special arrangement of carriers and labware on the worktable of the laboratory apparatus is necessary.

According to the invention, the method can be performed directly over an optional washing station, which is located on the worktable. In this way, the customer-specific equipment of the worktable with carriers does not have to be changed.

According to the invention, the method can be performed within a longer sequence of pipetting processes as an intermediate control step ("in process control"), e.g., over a washing station.

The method is preferably implemented as a single command line in control software for the end user. The pipetting process as a whole therefore does not have to be interrupted.

According to the invention, the connection and/or line quality between the tips or probes and the measuring circuit can be tested. Thus, for example, one can ascertain whether the coaxial cables, which are preferably used, are correctly connected, or whether the tips or probes are connected to the correct channels in a multichannel device. The quality of the shielding of the line connection can also be tested. The signal-to-noise ratio can also be ascertained. If the signal-to-noise ratio fulfills predefined criteria, the electrical connection is classified as qualitatively suitable for use in normal measuring operation.

All of these measures or analyses are used for the purpose of being able to make a connection statement.

According to the invention, faulty wiring, defective cable connections, and incorrectly installed tips or probes can be recognized easily and reliably.

According to the invention, disturbing influences of electrical noise sources such as motor noises or other electrical noises (e.g., coupling from a wireless LAN) can additionally be tested if desired.

According to the invention, the required tests can be performed within a few minutes even in the case of complex and highly integrated, multichannel systems.

According to the invention, the testing can be performed with respect to circuitry using special testing software or modules.

The testing software or modules are preferably part of the device or the laboratory apparatus.

The testing method of the invention is preferably implemented in a microprocessor of the device or the laboratory apparatus.

The testing software or modules can also be implemented separately, however, and can be designed for connection to the device or the laboratory apparatus.

The testing software or the module preferably uses commands (e.g., in the form of command lines), which are already implemented in the device or the laboratory apparatus for the liquid level detection (LLD). For the testing, only the respective suitable signal testing criterion or criteria, e.g., in the form of threshold values, are predefined and the desired speeds are set for the infeed movement.

According to the invention, the signal or the signals can be used in the digital circuit environment or in the analog environment for testing purposes. The analog signals are preferably converted into digital signals, in order to be related to the signal testing criterion or criteria therein and in order to be able to perform the analyses or judgments, respectively, in the digital circuit environment.

According to the invention, the testing of a channel can be executed in that different filters are used than during the normal capacitive detection of phase boundaries.

In a multichannel device, which uses a filtering method for separating two signals, a bandpass filter is preferably used for the second, slower signal to select a suitable frequency band, which allows reliable performance of the testing method.

Additionally or alternatively, the amplification factor (gain) of the signal processing can be set.

Additionally or alternatively, the sampling rate of the analog-digital conversion of the signal can also be adjusted to allow more reliable performance of the testing method.

The testing method of the invention can be performed in order to
do a quality test,
do an intermediate test,
do a test after completion of a manufacturing or installation step (e.g., by installation personnel),
do a field test after a repair or a routine service (e.g., by service personnel),
have a PQ (performance qualification) performed (e.g., by an end user), or
perform an "in process control" step within a sequence of pipetting steps (e.g., by an end user).

Through the invention, it is possible to provide universal devices and laboratory apparatuses, which deliver reliable testing results, for example, in the scope of one of the above-mentioned testing methods, in greatly varying situations and under greatly varying conditions.

BRIEF DESCRIPTION OF THE DRAWINGS

The device according to the invention, the laboratory apparatus according to the invention, and the method according to the invention will be explained in greater detail on the basis of schematic drawings of exemplary embodiments, which do not restrict the scope of the invention.

DESCRIPTION OF THE PREFERRED EMBODIMENTS

Advantageous embodiments of the invention are described hereafter, these being exemplary embodiments. These comprise both various implementations of the overall invention, and also assemblies and individual parts of the invention. Fundamentally, the described assemblies and individual parts of the various embodiments may be combined with one another, or the assemblies and individual parts of individual embodiments may be replaced by the assemblies and individual parts of other embodiments, respectively. The combinations formed in this case can require smaller adaptations, which are routine to any person skilled in the art and are therefore not described in greater detail, for example, to allow cooperation or interlocking of the assemblies and individual parts.

The term phase boundary is used for boundaries between two or more media, which have different dielectric constants. These are especially liquid-liquid and gas-liquid phase boundaries.

The term module is used here to describe a functional group which is implemented in hardware, software, or as a combination of hardware and software.

The term "identification" is used here for a code, a code word, a signal, a memory entry, or a flag, which is set.

Reference is made at various times in conjunction with the present invention to laboratory apparatuses 100. These are appliances, systems, facilities, apparatuses, handling centers, and the like, which are equipped with means for ascertaining a phase boundary. The device 110 according to the invention is an element or a component of such a laboratory apparatus 100. A laboratory apparatus 100 can comprise, for example, multiple identical devices 110 or multiple different devices 110.

The term "test" is used here for the testing of a device 110 or a laboratory apparatus 100. The term "testing method" refers to the performance of such a test.

The testing method of the invention can be performed in order to
do a quality test,
do an intermediate test,
do a test after completion of a manufacturing or installation step (e.g., by installation personnel),
do a field test after a repair or a routine service (e.g., by service personnel),
have a PQ (performance qualification) performed (e.g., by an end user), or
perform an "in process control" step within a sequence of pipetting steps (e.g., by an end user).

The invention is based on a large number of systematic experiments, in which the mutual influencing of the relative movement of a probe or a needle 3 in relation to the other probes or needles 3 of the device 110 has been studied. Greatly varying configurations and situations were experimentally studied. During these experiments, in each case the curves of the first signals $s1(t)$, or $s1d$ having short pulse width, and the second signal $s2(t)$, or $s2d$ having greater pulse width are processed, recorded, and analyzed by the measuring circuit 8 ($s1d$ and $s2d$ stand for the first and second signals in the digital circuit environment here).

The systematic experiments have had the result that the test can be performed in a dry manner. I.e., no special structures or apparatuses are necessary, such as the labware mentioned at the beginning, to perform tests. According to the invention, the testing can be performed by means of circuitry using special testing software or modules 20. The testing software or modules 20 can be a component of the device 110 or the laboratory apparatus 100. The testing software or modules 20 can also be implemented separately, however, and designed for connection to the device 110 or the laboratory apparatus 100 (e.g., via a bus 6).

Figure 4:
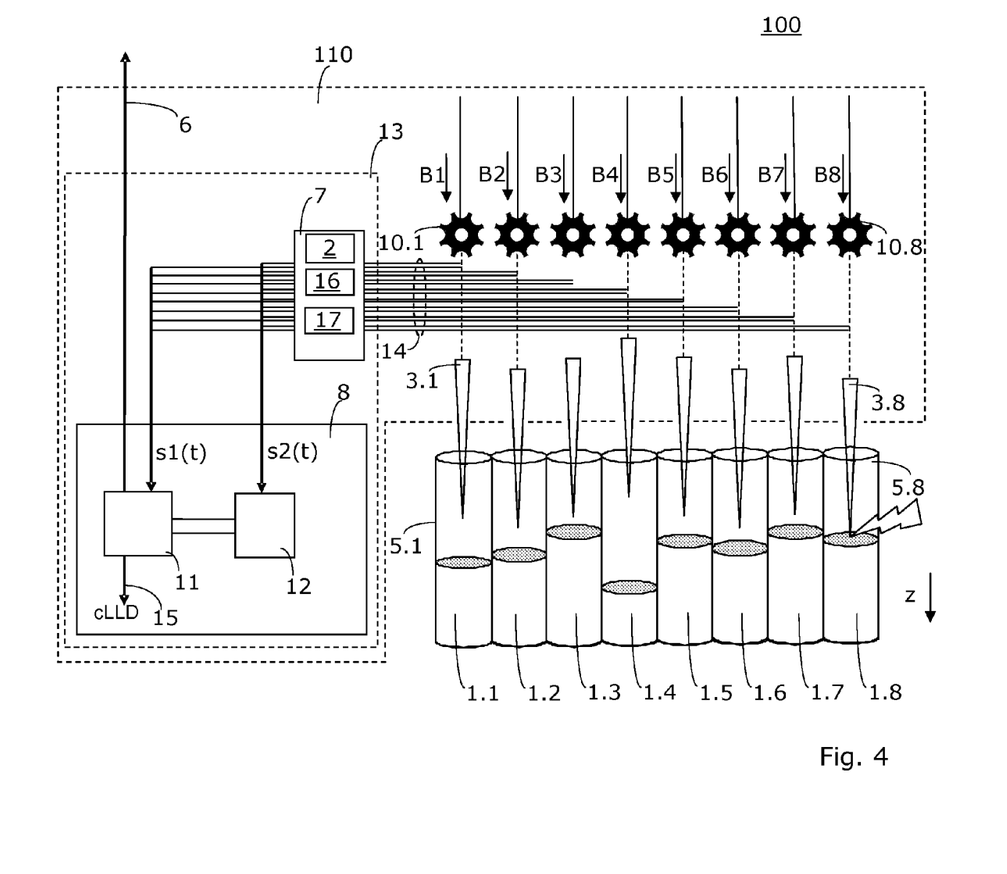
FIG. 4 shows a schematic side view of a multichannel, capacitively operating measuring device, which is suitable for performing a testing method according to the invention.

The method of the invention is especially designed for testing a preferably multichannel, capacitively operating measuring device 110, as is shown for exemplary purposes in FIG. 4. The method of the invention can also be used for testing a single-channel, capacitively operating measuring device 110, however.

FIG. 4 shows a schematic side view of a corresponding device 110 having a measuring circuit 13. The details described at the beginning may also be transferred to this device 110. Therefore, primarily the differences from the device 110 according to FIG. 1 are described hereafter. The laboratory apparatus 100 comprises multiple channels here (here n=8 channels). Each channel has infeed means $10.n$, which are shown here in simplified form by gear wheels. The infeed means $10.n$ generate a corresponding infeed movement Bn, as indicated by arrows, which point downward. The probes $3.n$ are preferably fed in individually by the infeed means $10n$. The probes $3.n$ plunge into liquid containers $5.n$, which are all filled with liquids $1.n$, for example. The respective phase boundaries are indicated by gray areas. At the moment shown, the probe $3.8$ has just plunged into the liquid $1.8$ of the liquid container $5.8$. The relative capacitance change which results in the eighth channel K.8 of the device 110 is shown here by a lightning symbol. The probes $3.n$ of the individual channels K.n are connected via individual lines 14 (preferably shielded lines) to the signal processing circuit 7 of the measuring circuit 13. This signal processing circuit 7 processes the signals s(t) of the individual channels K.n separately. Each signal s(t) of each channel K.n is filtered to obtain the corresponding first and second signals $s1(t)$ and $s2(t)$. I.e., in total eight first signals $s1(t)$ and eight second signals $s2(t)$ are obtained per measuring cycle, if a device 110 having n=8 channels is observed. The probes $3.n$ are charged and discharged at a suitable frequency (preferably in the range of several hundred kilohertz) by the charging/discharging circuit 2.

The device 110 comprises a controller module 8, as shown. The controller module 8 comprises a comparator module, which is implemented here in this device by a first microprocessor 11. The comparator module is designed, or the first microprocessor 11 is programmed, respectively, so that it ascertains whether the first signals $s1(t)$ of the individual channels K.n reach first threshold values T1. This principle was already described above. However, the comparator module, or the first microprocessor 11, respectively, processes all first signals s1(t) of the eight channels K.n successively in a staggered manner here.

Instead of one or two signals, the invention can also be based on the analysis/processing of multiple signals.

Furthermore, the controller module 8 comprises a processing module, which is implemented here in this embodiment by a second microprocessor 12. The processing module is preferably designed, or the second microprocessor 12 is programmed, respectively, so that it ascertains whether the second signals s2(t) fulfill predefined second signal criteria. This principle was already described at the beginning. The processing module, or the second microprocessor 12, respectively, processes all second signals s2(t) of the eight channels in a staggered manner here. If both signals s1(t) and s2(t) fulfill the criteria for one of the eight channels, it is presumed that in this channel K.n, the probe 3.n has reached the phase boundary to the liquid 1.n. In the present case, an identification (e.g., in the form of a signal or code) was output for the eighth channel K.8, because the probe 3.8 has just plunged into the liquid 1.8 in the container 5.8. This identification can be output, e.g., via an interface (cLLD) 15. The laboratory apparatus 100 can make decisions, trigger reactions, or the like on the basis of this identification, for example.

The device 110, in which the testing method according to the invention is applied, therefore comprises, expressed in summary, one probe 3.n per channel K.n (n being a whole number greater than or equal to 1), which is fed into a liquid container 5.n of the corresponding channel K.n. During the infeed (indicated by the infeed movement Bn), a signal (e.g., s1(t)) or first signals s1(t) having short pulse width and second signals s2(t) having greater pulse width are processed by a measuring circuit 13, to detect a phase boundary between two media in the liquid container 5.n of the corresponding channels K.n.

Figure 5A:
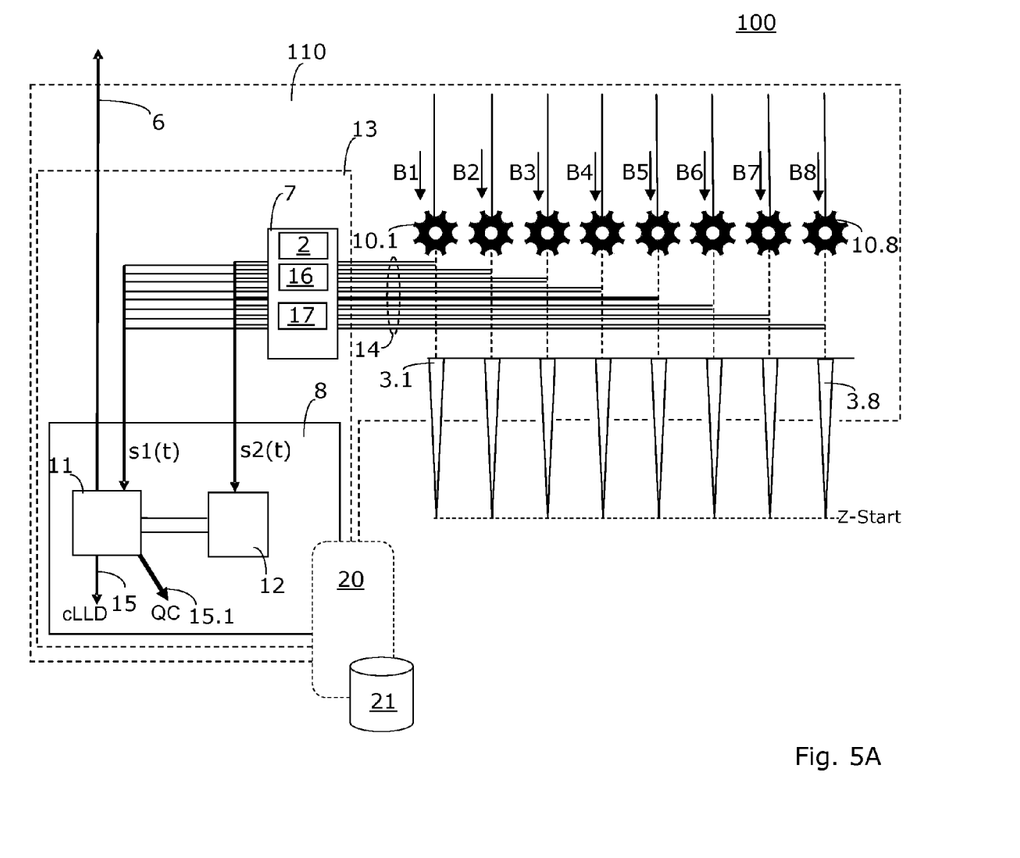
FIG. 5A shows a schematic side view of the measuring device according to FIG. 4 before the performance of a testing method according to the invention.

FIG. 5A indicates that the testing method of the invention is executed in a dry manner. I.e., no probes or tips 3.n are plunged into any type of media 1.n during the performance of the testing method. No special measurement structures or other devices (labware) are used either. The probes 3.n are therefore shown freely floating in FIG. 5.

The testing method typically begins from a position in which all probes 3.n are located adjacent to one another on one level (called Z-start here). In a multichannel arrangement, the following steps are executed for the testing.

An infeed movement B2 of an individual probe 3.2 of a single channel K.2 of the measuring device 110 is executed, while the other probes 3.1, 3.3 to 3.8 of the other channels of the measuring device 110 do not move. The infeed movement B2 of the individual probe 3.2 is caused by the infeed means 10.2. The infeed movement B2 occurs at a predefined speed vz. During the execution of this infeed movement B2, the first signal s1(t), preferably a signal having short pulse width, and/or the second signal s2(t), preferably a signal having greater pulse width, of at least one of the channels of the measuring device 110 are analyzed.

The goal of this analysis is the provision of a statement (e.g., in the form of an identification or a memory entry) about the electrical connection of the individual probe or probes 3.n of the channel or channels K.n of the measuring device 110 to the measuring circuit 13. The statement about the presence and/or the quality of a connection is referred to here as a connection statement.

An identification (e.g., in the form of a signal or code) is preferably output either only for the one channel whose probe 3.2 was currently moved (referred to here as the "moved" channel), or for all other channels (referred to here as the "non-moved" channels). This identification can be output, e.g., via an interface (QC) 15.1. The laboratory apparatus 100 can make decisions, trigger reactions, or the like, for example, on the basis of this identification.

Figure 6A:
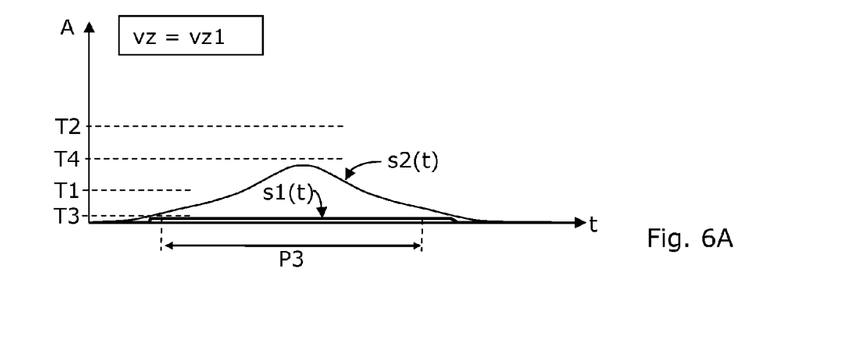
FIG. 6A shows an amplitude-time graph in which two signals are shown in simplified form, to be able to describe the application of signal testing criteria according to the invention.

FIG. 6A shows a simplified curve of the two signals s1(t) and s2(t), which results when, in a device 110 which provides two signals using a filter method, the probe 3.2 is slowly fed in at a speed vz1 in the Z direction, while the other probes 3.1, 3.3-3.8 are not moved. The rapid signal s1(t) hardly changes. It remains in an amplitude range below T3. T3 is considered here to be the second signal testing criterion. For comparison, the threshold values T1 and T2 according to FIG. 3 are also shown in FIG. 6A. The slow signal s2(t) clearly responds, since it operates at a lower frequency and therefore the capacitance change is correspondingly greater. However, it remains in an amplitude range below T4 here. T4 is considered here to be the first signal testing criterion.

Figure 6B:
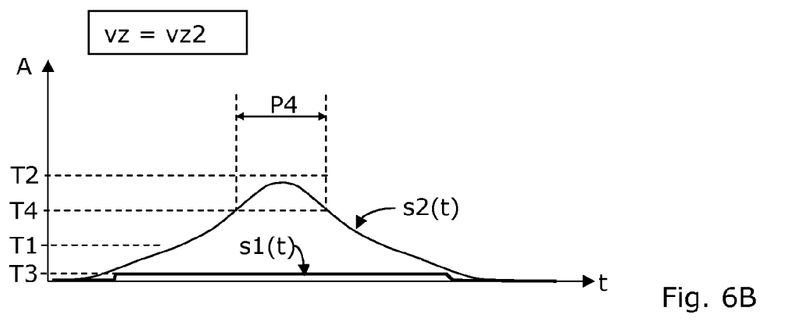
FIG. 6B shows another schematic amplitude-time graph in which two signals are shown in simplified form, to be able to describe the application of signal testing criteria according to the invention.

FIG. 6B shows a simplified curve of the two signals s1(t) and s2(t), which results when the probe 3.2 is fed in rapidly at a speed vz2 (vz2>vz1) in the Z direction, while the other probes 3.1, 3.3-3.8 are not moved. The rapid signal s1(t) changes somewhat more strongly than during the slow movement. However, it also remains here in an amplitude range below T3. For comparison, the threshold values T1 and T2 according to FIG. 3 are also shown in FIG. 6B. The slow signal s2(t) still responds more clearly. The amplitude clearly exceeds the threshold value T4.

However, for example, the first signal testing criterion can also comprise the pulse duration P4 or flank slope ST of the measurable increase of the second signal s2(t) during a rapid movement of a probe 3.1-3.8. The first signal testing criterion preferably comprises both the threshold value T4 and also the pulse duration P4.

A rapid movement of a single probe 3.n can be used to be able to detect on the basis of the reactions of the measuring circuit 13 whether the electrical connection (by means of lines 14) between the probe 3.n (with n=1) or the individual probes 3.n (with n>1) and the measuring circuit 13 functions. If the measuring circuit 13 detects a slow signal s2(t) on the channel K.2, whose probe 3.2 was moved rapidly (moved probe), that fulfills a predefined first signal testing criterion, then the electrical connection 14 between this moved probe 3.2 and the measuring circuit 13 is intact. In addition, in a multichannel device, the signals of the other probes 3.1, 3.3-3.8 (non-moved probes) can also be analyzed to test whether corresponding reactions of the slow signals s2(t) are shown here.

Figure 5B:
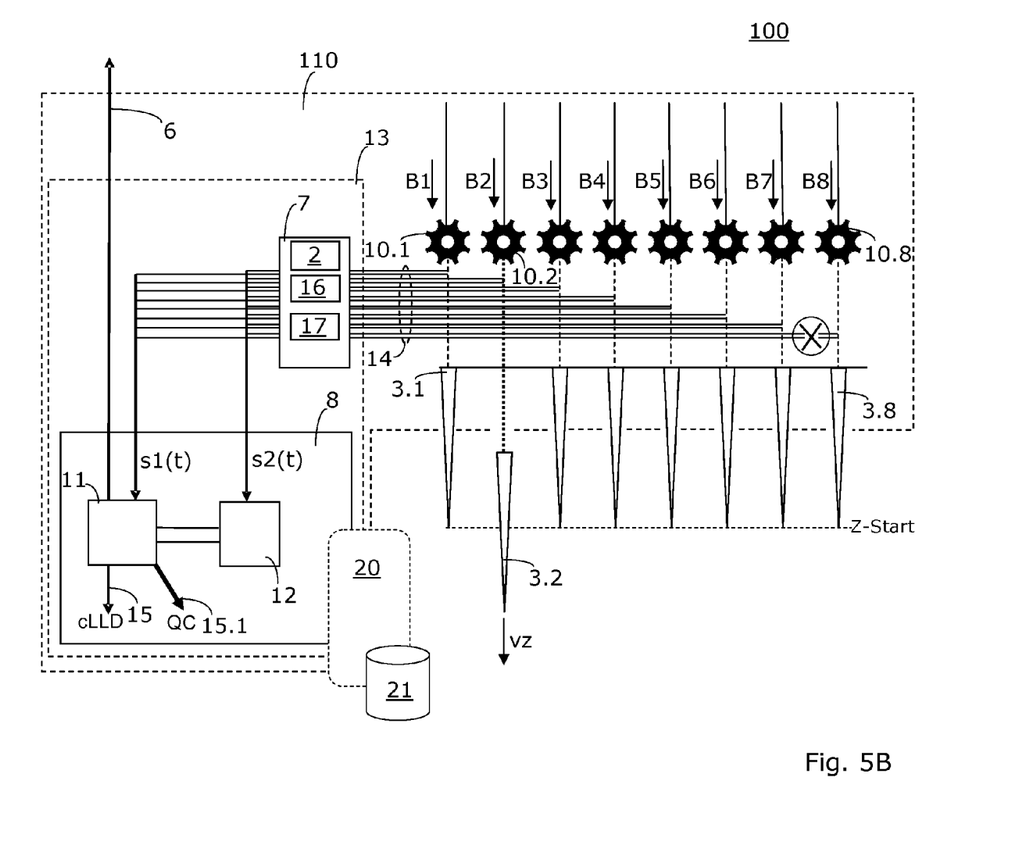
FIG. 5B shows a schematic side view of the measuring device according to FIG. 4 during the performance of a testing method according to the invention.

FIG. 5B indicates that the electrical connection 14 between the probe 3.8 and the measuring circuit 13 is interrupted. A cable break may exist here, for example, in the region identified by a large X.

Figure 7:
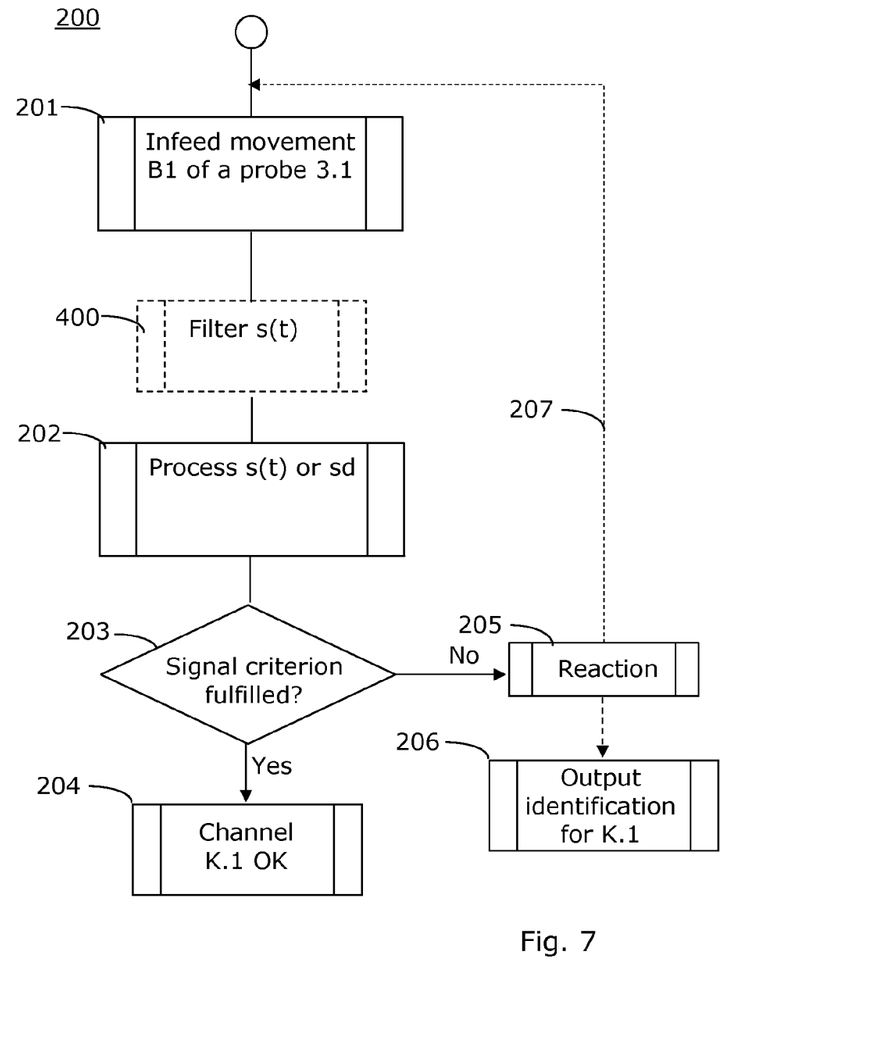
FIG. 7 shows a schematic flow chart of the functional principle of a testing method according to the invention.

FIG. 7 shows a schematic flow chart which illustrates the essential steps of the (connection) testing method 200 of a single-channel measuring device 110. This (connection) testing method 200 can also be applied for testing a single channel in a multichannel measuring device 110. To test the measuring device 110, the following steps are executed. An infeed movement B1 of the probe 3.1 of the channel K.1 is executed (FIG. 7, step 201). This probe 3.1 therefore execute a relative movement in relation to a nonmoving reference surface, a nonmoving reference object (e.g., the worktable) or reference body of the measuring device 110. The measuring circuit 13 processes the output signal s(t) (FIG. 7, step 202). Optionally, in the exemplary embodiment shown, this signal s(t) can be filtered in order to be able to analyze a suitable frequency band, for example (FIG. 7, optional step 400). For example, in the scope of the (connection) testing method 200, the signal s(t), or sd, of the channel K.1 of the measuring device 110 is analyzed here (FIG. 7, step 202), to be able to make a statement (e.g., in the form of an identification or a memory entry) about the electrical connection 14 between the probe 3.1 and the measuring circuit 13. During the processing of the signal s(t) (FIG. 7, step 202), a signal testing criterion (FIG. 7, step 203) or a combination of signal testing criteria can be applied. If the signal testing criterion or criteria are fulfilled, then the channel K.1 can be marked as OK, for example (FIG. 7, step 204). Otherwise, the method 200 branches in the direction of step 205 in order to trigger a reaction.

One or more reactions are conceivable here and in the other methods. E.g., the method 200 can branch back (path 207) in order to run through the test 200 again. For example, it is also possible to output a special identification for the corresponding channel (channel K.1 here) as a reaction (FIG. 7, step 206). For example, it is also possible to run through the test 200 multiple times (e.g., three times), before a special identification for the corresponding channel (here channel K.1) is output in step 206.

Additional tests can also be performed as a reaction.

Figure 8:
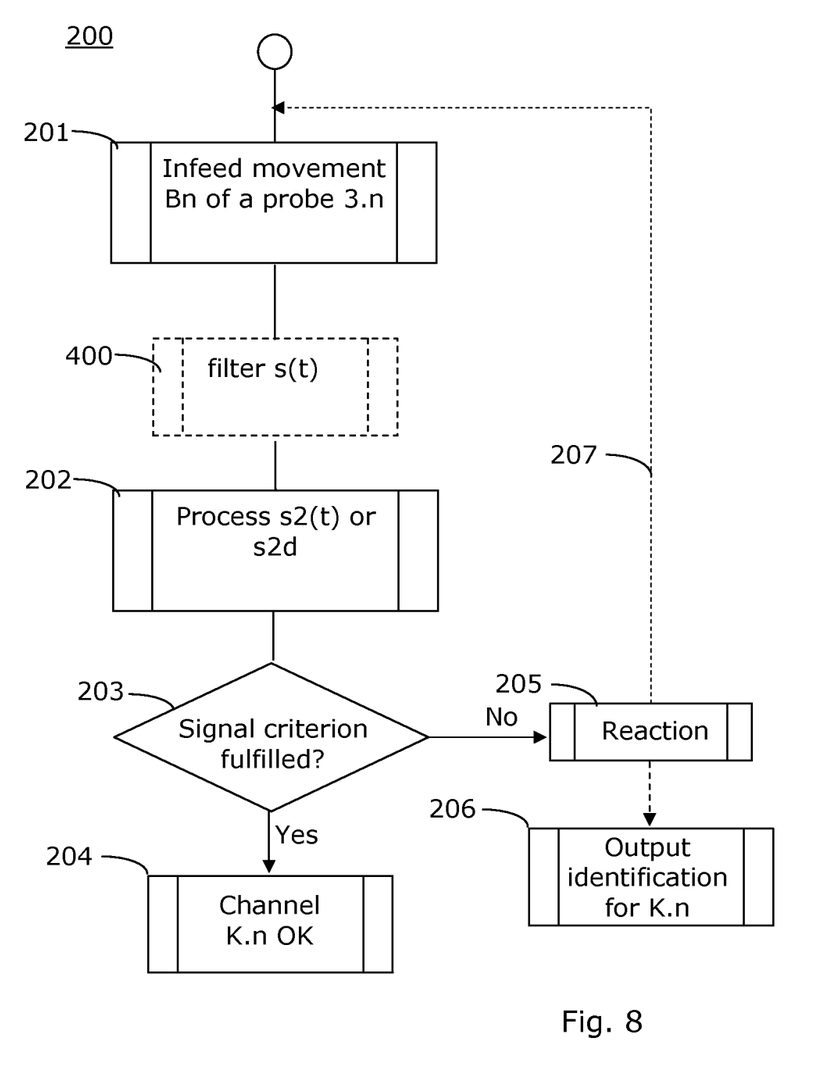
FIG. 8 shows a schematic flow chart of the functional principle of a testing method according to the invention.

FIG. 8 shows a schematic flow chart which illustrates the essential steps of the (connection) testing method 200 of a multichannel measuring device 110. To test the measuring device 110, the following steps are executed. An infeed movement Bn of a probe 3.n of a single channel K.n is executed (FIG. 8, step 201), while the other probes of the other channels K.n are not moved. The measuring circuit 13 processes the output signal s(t) in that, in the exemplary embodiment shown, it filters this signal s(t) (FIG. 8, step 400). The optional filtering procedure provides, for example, the second signal s2(t) here, or, after an analog-digital conversion, the signal std. The filtering 400 is preferably performed, in all embodiments which are based on a filtering method, through the use of hardware or software filters 16, 17, which are seated, e.g., in the signal processing circuit 7 of the measuring circuit 13. For example, in the scope of the (connection) testing method 200, the second signal s2(t), or s2d, is processed by means of one of the channels K.n of the measuring device 110 here (FIG. 8, step 202), in order to be able to make a statement (e.g., in the form of an identification or a memory entry) about the electrical connection 14 between at least one of the probes 3.n and the measuring circuit 13. One or more reactions are also conceivable here, as described above in conjunction with FIG. 7.

Figure 9:
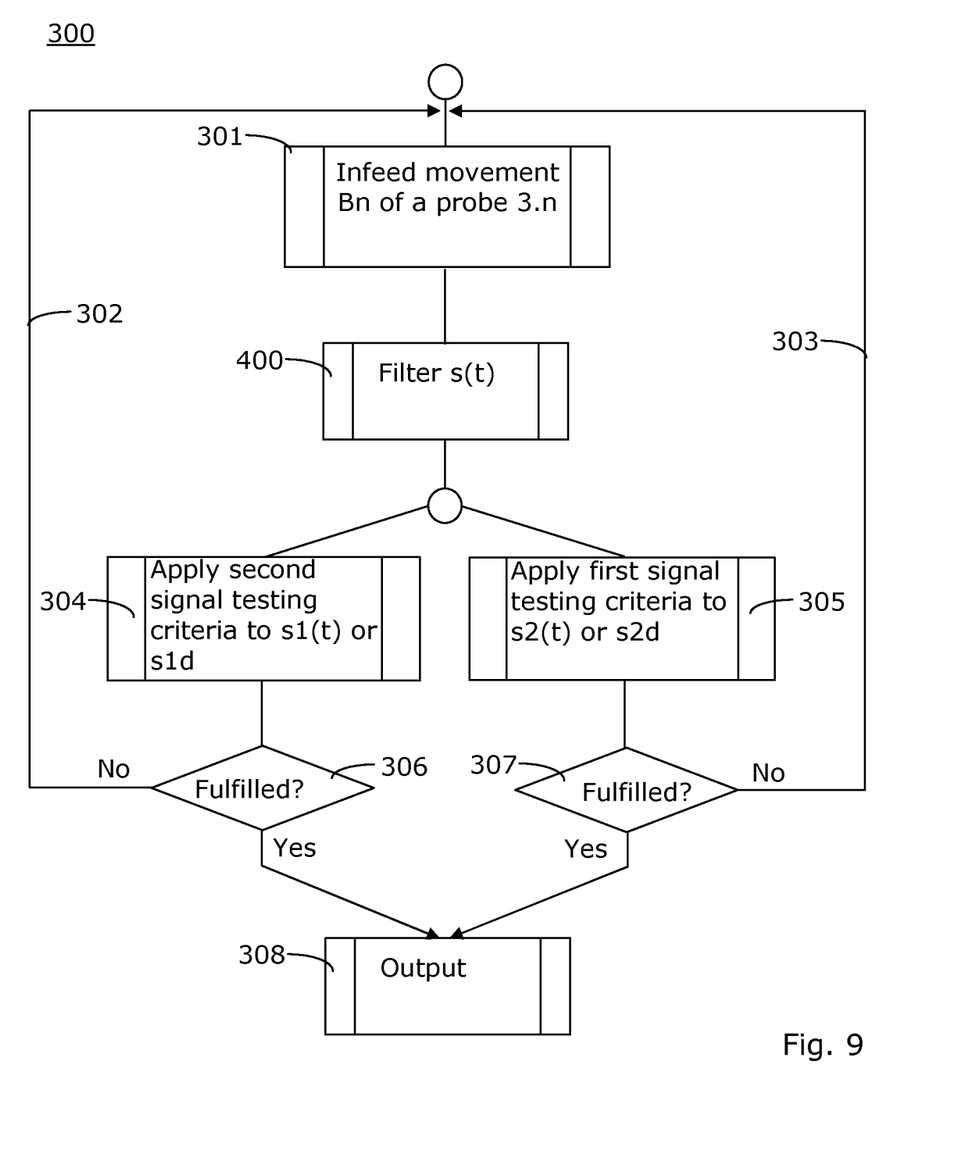
FIG. 9 shows a schematic flow chart of the functional principle of the signal analysis of a device according to the invention.

Details of another method 300 for processing the output signal s(t) and for the parallel analysis of the first signals s1(t), s1d and the second signal s2(t), s2d can be inferred from FIG. 9. The method 300 according to FIG. 9 may be applied to single-channel and multichannel devices 100. The method 300 also begins with the infeed movement 301 of (at least) one probe 3.n. The infeed movement 301 can, but does not have to, differ from the infeed movement 201. In a downstream step 400, the analog output signal s(t) is filtered with application of a filtering method to obtain the two mentioned analog signals s1(t) and s2(t). The filtering 400 is preferably performed in all embodiments by the use of hardware or software filters 16, 17, which are seated, e.g., in the signal processing circuit 7 of the measuring circuit 13. The two analog signals s1(t) and s2(t) are then preferably converted by analog-digital converters into the corresponding signals s1d and s2d.

Then, preferably in all embodiments of the invention at the same time, the signal testing criteria are applied to the first signal s1(t), or s1d and to the second signal s2(t), or s2d, as indicated by the processes 304 and 305. If the signal testing criteria are fulfilled, the corresponding decision process 306 or 307 provides a corresponding (success) signal (the two paths which are identified by a "yes" here). For example, if all signal testing criteria are fulfilled, a process 308 can output or store an identification (e.g., a signal or a code). If one signal testing criterion or multiple signal testing criteria are not fulfilled, the process branches back to the beginning, for example, as shown by the two paths 302, 303 (the two paths which are identified by a no here).

The pass through the method 300 can be repeated multiple times depending on the embodiment, as described in conjunction with FIG. 7.

Preferably, during the execution of the infeed movement Bn (FIG. 7 or FIG. 8, step 201), at least one probe 3.n of a channel K.n is repeatedly electrically charged and discharged and the output signal s(t) at this probe 3.n is tapped and processed (FIG. 7, step 202), or the output signal s(t) is filtered (FIG. 8, step 400) and then processed (FIG. 8, step 202).

A corresponding signal testing criterion is preferably applied for the processing (FIG. 7, step 202) of the output signal s(t), sd.

A corresponding signal testing criterion (called the second signal testing criterion) is preferably applied for processing (FIG. 8, step 202) the first signal s1(t), s1d. A corresponding other signal testing criterion (called the first signal testing criterion) is applied for processing (FIG. 8, step 202) the second signal s2(t), s2d.

It is queried or ascertained during the processing (FIG. 7, step 202; FIG. 8, step 202; FIG. 9, steps 304, 305) whether the signals s(t), sd, s1(t), s1d, s2(t), s2d fulfill the corresponding signal testing criteria. If the signal testing criterion or criteria are fulfilled, the corresponding channel K.n is identified as an order (FIG. 7, step 204; FIG. 8, step 204; FIG. 9, step 308). If one of the signal testing criteria or multiple of the criteria are not fulfilled, the method according to FIG. 8 branches and a reaction occurs (FIG. 7, step 205; FIG. 8, step 205; FIG. 9, path 302, 303).

The reaction can appear different depending on the embodiment. Thus, for example, the (connection testing) method 200 can branch back to the beginning (path 207 in FIG. 7 or FIG. 8), to restart the method 200, or the method 200 can output a statement (e.g., in the form of an identification) for the faulty channel K.n (e.g., via the QC output 15.1) or, e.g., store it in a storage medium 21 (FIG. 7 or FIG. 8, step 206).

Depending on the (connection testing) method 200, a cable break is already recognizable if, e.g., the probe 3.8 is moved rapidly downward. All channels, except for the eighth channel, then provide more or less strong signals s2(t), which fulfill the first signal testing criterion. Therefore, a first index that something does not appear to be right with the eighth channel is already obtained upon the rapid movement of one of the other probes.

A more precise conclusion is obtained in that each of the probes 3.n of a multichannel device 110 are successively moved rapidly, while the respective other probes are not moved. At latest when the probe 3.8 is moved rapidly downward, it will be shown that the second signal s2(t) of the eighth channel does not fulfill the first signal testing criterion. The faulty connection of the eighth channel is thus unambiguously identified.

In summary, it can be determined that through the observation/processing of the second signal s2(t) during the execution of a rapid infeed movement using at least one of the probes 3.n, it may be ascertained whether there are connection problems in one or more of the channels K.n.

The first rapid signal s1(t) can preferably also be used for the testing. An observation/analysis of the first signal s1(t) during the execution of a slow infeed movement of at least one of the probes 3.n is preferably stopped here. As indicated in FIG. 6A, the first signal s1(t) shows a small amplitude change. If such a small amplitude change is detected during the slow movement, the noise on the channels, or the noise of the entire signal processing chain including the measuring circuit 13, respectively, is negligible, because there is a sufficient signal-to-noise ratio. In contrast, if a change of the first signal s1(t) which exceeds a threshold value T3 exists during the slow movement, interfering noise exists, which can induce problems in the detection of a phase boundary during the performance of a measurement. In this case, the noise is apparently so strong that it significantly overlays and interferes with the signal s1(t), which must actually be relatively small during a slow infeed movement of a probe 3.n. In this case, the signal-to-noise ratio is excessively small.

During the observation/processing of the first signals s1(t), a so-called second signal testing criterion can be applied. In a simple embodiment of the invention, the second signal testing criterion is the threshold value T3, which is predefined. If a first signal s1(t) exceeds the threshold value T3, the noise is considered to be interfering or critical and the corresponding channel K.n is marked as faulty.

However, the second signal testing criterion can also comprise, for example, the pulse duration P3 or flank slope ST of the measurable increase of the first signal s1(t) during a slow movement of a probe 3.n. The second signal testing criterion preferably comprises both the threshold value T3 and also the pulse duration P3.

The testing method 200 preferably comprises an offset calibration for the signal s(t) or, in embodiments having filtering methods, both for the rapid first signal s1(t) and also the slow second signal s2(t). If this offset calibration does not deliver positive results, this may be because the device 110 has excessively strong noise. In this case, in a multichannel device 110, individual probes 3.n may be moved slowly successively, while the respective other probes are stationary. By observing/analyzing the first signals s1(t) during the execution of the slow infeed movement, it can be ascertained whether the first signals s1(t) fulfill the second or a special third signal testing criterion. If this is not the case, it has been shown that excessively strong noise exists.

After the execution of an offset calibration or after the execution of a noise recognition via the analysis of the output signal s(t) or the first signals s1(t), as described, the connections 14 with respect to circuitry between the probes 3.n and the measuring circuit 13 can be tested. This connection test (testing method 200) is performed, as described, by alternating rapid movement of the probe 3.n, while the other probes 3.n are not moved.

The sequence of these tests can also be selected so that the execution of a noise recognition is only performed after the connection test (testing method 200).

The noise recognition via the analysis of the first signals s1(t) and the detection of connection problems with respect to circuitry via the analysis of the second signals s2(t) can also be executed separately, i.e., independently of one another.

Both the noise recognition via the analysis of the first signals s1(t) and also the detection of connection problems with respect to circuitry via the analysis of the second signals s2(t) (called connection test 200) can each be performed so that only the signals s1(t) and s2(t) of the moved probe (e.g., the probe 3.2) are observed and analyzed. However, both testing methods may also be executed in that in addition the signals s1(t) and s2(t) of other channels (non-moved channels) are also observed and analyzed with respect to the mentioned signal testing criteria, or further additional signal testing criteria.

The following testing method for the detection of connection problems with respect to circuitry, i.e., for the connection test 200, is preferably used in all embodiments, in a multichannel device 110:

1. One of the probes 3.n is moved rapidly (for instance downward) at vz2 and the signals s2(t) are analyzed;
   a. for each channel K.n having moved probe 3.n (moved channel):
      i. If the slow signal s2(t) of this "moved" channel K.n does not fulfill the first signal testing criterion (e.g., s2(t>T4 and/or s2(t)>P4), then this "moved" channel K.n is classified as not connected (then, for example, a corresponding identification is output via the QC output 15.1 or a memory entry is performed);
   b. for each "non-moved" channel:
      i. If the rapid signal s1(t) and/or the slow signal s2(t) of one of these channels K.n does not fulfill the corresponding second signal testing criteria or the first signal testing criteria, this "non-moved" channel K.n is classified as "critical" (e.g., because the installation of the coaxial cable is damaged). Optionally, in a following step, this result can be retested once again (e.g., in that the probe of this critical channel K.n is moved and the slow signal s2(t) is tested in the meantime).

Optionally, it can also be tested whether the slow signal s2(t) of the "moved" channel K.n lies outside a measured value window or outside a criteria range. If this is the case, this "moved" channel K.n is classified as "critical" (for example, a corresponding identification is then output via the QC output 15.1 or a memory entry is performed).

Optionally, it can also be tested whether the rapid signal s1(t) of the "moved" channel K.n does not fulfill the corresponding signal testing criteria. If this is the case, this "moved" channel K.n is classified as "critical" (for example, a corresponding identification is then output via the QC output 15.1 or a memory entry is performed).

Depending on the situation, individual channels K.n can be classified as not connected, or they can be classified as the channel K.n which has not passed a test (classification as critical channel). In the latter case, the method 200 can be completely repeated, for example (FIG. 7 or FIG. 8, path 207), a test of only the critical channel can be performed, or additional tests can be performed.

In addition to the above-described testing methods, interference sources can be tested as follows:

a. For each channel K.n having moved probe 3.n:
   i. Slowly moving the probe 3.n at a speed which is preferably less than vz1. If the rapid signal s1(t) of this "moved" channel K.n does not fulfill the second or a third signal testing criterion (s1(t)>T3 and/or s1(t)>P3), then the test is classified as not passed (a corresponding identification is then output via the QC output 15.1 or a memory entry is performed, for example).
   ii. Slowing moving the probe 3.n at a speed which is preferably less than vz1. If the rapid signal s1(t) of this "moved" channel fulfills the second or a third signal testing criterion (s1(t)<T3 and/or s1(t)<P3), then the test is classified as passed (a corresponding identification is then output via the QC output 15.1 or a memory entry is performed, for example).

Depending on the identification or memory entry, which was performed after a test, the user of the device 110 can be requested to remedy an error or to execute further steps via an output unit (e.g., a display screen or a speech output).

If the test has the result that the offset calibration and/or the carrying out of a noise recognition by means of an analysis of the output signal s(t) or the first signal S1(t), as described, have/has not occurred because of excessive noise, the grounding of the motor or motors and/or the grounding of the laboratory apparatus 100 can be tested. One can also attempt to turn off adjacent devices or, e.g., lamps or other possible interference sources, which can cause electrical scattering. The testing method 200 can then be entirely or partially performed again to test the success of the described measures.

If the test has the result that the offset calibration and/or the carrying out of a noise recognition have/has not occurred because of excessive significant noise, the user can then, for example, be requested to replace possibly faulty tips or probes 3.n in the channels K.n.

If the test has the result that the offset calibration and/or the carrying out of a noise recognition have/has not occurred because of excessive significant noise, the user can then be requested, for example, to replace the measuring circuit 13 (e.g., by exchanging the circuit board which comprises the measuring circuit 13).

If the connection test 200 has the result that a specific channel K.n is not connected or is not connected correctly, this critical channel K.n can be manually or automatically checked. This checking can be part of the reaction 205. The connection test can then be entirely or partially performed again (FIG. 7 or FIG. 8, path 207).

According to the invention, the testing can be performed with respect to circuitry using testing software or one or more special modules 20. The testing software or modules 20 can be a component of the device 110 or the laboratory apparatus 100. In FIGS. 5A and 5B, the testing method is schematically identified by a block 20. The block 20 is preferably implemented in a microprocessor (e.g., in the microprocessor 11 and/or 12) of the measuring circuit 13.

The block 20 is connected with respect to circuitry to the most important components of the device 110 or the laboratory apparatus 100 in such a manner that it is capable of triggering testing sequences, receiving the signals s1(t) or s1d and s2(t) or s2d, processing them, and outputting results (e.g. identifications) or performing the mentioned memory entries.

For this purpose, the device 110 or the laboratory apparatus 100 can comprise a storage medium 21. This storage medium 21 can be designed as an event memory, in which the results of the tests are stored and made accessible for later access.

The device 110 or the laboratory apparatus 100 preferably comprises a bus 6, which allows an exchange of data. Via this bus 6, for example, the laboratory apparatus 100 can request information from the storage medium 21. It is thus made possible for processes which are executed by the laboratory apparatus 100 to be able to be adapted to the current situation. E.g., a critical channel K.n or a probe 3.n, which was classified as not connected, can be excluded from the process to avoid errors.

Instead of the two separate microprocessors 11 and 12, a shared, very high-performance processor can also be used in the various embodiments. The block 20 is preferably implemented in this high-performance processor.

In the various embodiments of the invention, decisions are preferably made by suitable software (represented by the block 20) and sequences are controlled/monitored by the software (represented by the block 20). For this purpose, the software accepts information and/or signal values from the controller module 8. On the basis of rules, which are predefined, sequences can then be controlled/monitored, analyses can be performed, and decisions can be made if necessary. Thus, for example, the software can decide whether a probe 3.n (e.g., in the form of a needle or pipette tip) is to be marked as critical, e.g., because it has been recognized to be faulty according to the invention. The software can also decide whether a channel K.n is to be completely turned off, or whether in case of a malfunction, e.g., operating personnel are to be called.

LIST OF REFERENCE NUMERALS

| | |
|---|---|
| liquid | 1 (in general 1.n) |
| liquids of individual channels | 1.1-1.8 |
| electronic charging/discharging circuit | 2 |
| probe (e.g., pipette tip) in general | 3 (in general 3.n) |
| probe (e.g., pipette tip) which can be fed in | 3.1-3.8 |
| base plate | 4 |
| liquid container in general | 5 or (in general 5.n) |
| liquid containers of single channels | 5.1-5.8 |
| bus | 6 |
| signal processing circuit | 7 |
| controller module | 8 |
| infeed means (e.g., DC motors) | 10.1-10.8 (in general 10.n) |
| first microprocessor | 11 |
| second microprocessor | 12 |
| (measuring) circuit | 13 |
| (connection) lines | 14 |
| (cLLD) interface | 15 |
| (QC) interface | 15.1 |
| filter | 16 |
| filter | 17 |
| block (module/software) for performing the testing method | 20 |
| storage medium | 21 |
| laboratory apparatus | 100 |
| device | 110 |
| (connection testing) method | 200 |
| infeed movement | 201 |
| analysis | 202 |
| testing whether signal testing criterion is fulfilled | 203 |
| channel in order | 204 |
| reaction | 205 |
| output/identification output | 206 |
| path | 207 |
| further method | 300 |
| infeed movement | 301 |
| paths | 302, 303 |
| apply second signal testing criteria to s1(t) | 304 |
| apply first signal testing criteria to s2(t) | 305 |
| first signal testing criteria fulfilled | 306 |
| second signal testing criteria fulfilled | 307 |
| output | 308 |
| filter output signal s(t) | 400 |
| amplitude | A |
| infeed movement in general | B |
| infeed movement of single channels | B1-B8 (in general Bn) |
| scattering capacitance | $C_{tip/tip}$ |
| coupling capacitor | $C_{coupl}$ |
| capacitance between probe and liquid | $C_{tip/liq}$ |
| capacitance between the probe and the worktable | $C_{tip/worktable}$ |
| channel | K.n, K.m |
| number/numbering of the channels | n, m |
| pulse width/pulse duration | P1, P2, P3, P4 |
| slope | ST |
| output signal | s(t) |
| output signal digitized | sd |
| first signal | s1(t) |
| first signal digitized | s1d |
| second signal | s2(t) |
| second signal digitized | s2d |
| axis | z |
| starting position | Z-Start |
| time | t |
| first threshold value | T1 |
| second threshold value | T2 |

-continued

| | |
|---|---|
| further threshold value | T3 |
| further threshold value | T4 |

The invention claimed is:

1. A method for the contactless testing of a capacitively operating measuring device, said measuring device comprising:
   at least one channel having a probe which can be fed into a liquid container of the corresponding channel, and
   a measuring circuit, wherein during an infeed movement of the probe, at least one signal is generated, which is processed by the measuring circuit for detecting a phase boundary between two media in the liquid container of the corresponding channel,
   wherein the method is a dry method comprising the following steps for testing the capacitively operating measuring device:
   (a.) executing an infeed movement of a probe of a channel without touching a liquid, in the measuring device, thereby generating at least one signal,
   (b.) processing and analyzing said signal of this one channel or another channel using the measuring circuit,
   (c.) providing a connection statement about the electrical connection between the one moved probe and the measuring circuit based on the analysis in step (b.) or another channel and the measuring circuit.

2. The method according to claim 1, wherein the measuring device is a single-channel measuring device, comprising one channel with one probe which is feedable into a liquid container of said channel, a corresponding signal testing criterion being applied during the processing of the signal.

3. The method according to claim 1, wherein the measuring device is a multichannel measuring device, comprising more than one channel having one probe in each channel, each probe being feedable into a liquid container of the corresponding channel, wherein in said multichannel measuring device a filtering method is applied, to obtain a first signal and a second signal from the signal.

4. The method according to claim 3, wherein during the processing of the first signal, a corresponding signal testing criterion is applied, and for the analysis of the second signal, a corresponding other signal testing criterion is applied.

5. The method according to claim 3, wherein during the processing, the signal of the channel of the measuring device is analyzed, whose probe was fed in during step (a.).

6. The method according to claim 3, wherein during the processing, the first signal and/or the second signal of at least one of the non-moved channels of the measuring device is analyzed.

7. The method according to claim 1, wherein the connection statement permits an evaluation of whether the electrical connection between the one probe and the measuring circuit is present and/or qualitatively suitable.

8. The method according to claim 1, wherein during the execution of the infeed movement, the probe of the one channel is repeatedly electrically charged and discharged.

9. The method according to claim 1, wherein during the processing, the signal is analyzed with application of a signal testing criterion to make a statement about noise.

10. The method according to claim 1, wherein the method is performed in order to
    do a quality test,
    an intermediate test,
    a test after completion of a manufacturing or installation step,
    a field test after a repair or a routine service, or to
    perform a performance qualification, or to
    perform an in process control step within a sequence of pipetting steps.

11. The method according to claim 1, wherein the infeed movement for ascertaining the connection statement is performed rapidly, the speed of the infeed movement preferably being greater than 200 mm/s.

12. The method according to claim 1, wherein the infeed movement is performed slowly to ascertain a statement about noise, the speed of the infeed movement preferably being less than 200 mm/s.

13. A device having at least one channel, the channel being configured for detecting the phase boundary between media in a liquid container of the channel, and the channel comprising a probe, which can be fed in the direction of the phase boundary, and the device comprising a measuring circuit, which processes a signal of the probe to detect a capacitance change,
    wherein the device further comprises:
    a testing module, which is configured for executing the following steps of a dry testing method:
    executing an infeed movement of the probe without touching a liquid for generating a signal,
    performing the processing and analysis of the signal of a channel of the measuring device, and
    providing a connection statement about the electrical connection (14) between the probe and the measuring circuit based on the analysis of the signal.

14. The device according to claim 13, characterized in that it comprises at least one microprocessor, in which the testing module is implemented.

15. The device according to claim 13, characterized in that it comprises a storage medium to be able to store
    the connection statement and/or
    an identification and/or
    a code,
    provided by the testing module.

16. The device according to claim 13, characterized in that it comprises an electronic charging/discharging circuit, to be able to charge and discharge the probe multiple times.

17. The device according to claim 13, characterized in that it is configured as a multichannel measuring device comprising more than one channel having one probe in each channel, each probe being feedable into a liquid container of the corresponding channel.

18. The device according to claim 17, characterized in that it is configured for applying a filter method to separate the signal into at least one first signal and one second signal.

19. A laboratory apparatus, which comprises at least one device according to claim 13.

* * * * *